United States Patent
Page et al.

(10) Patent No.: US 9,765,308 B2
(45) Date of Patent: *Sep. 19, 2017

(54) AROMATIC PRENYLTRANSFERASE FROM CANNABIS

(71) Applicants: National Research Council of Canada, Ottawa (CA); University of Saskatchewan, Saskatoon (CA)

(72) Inventors: Jonathan E. Page, Vancouver (CA); Zakia Boubakir, Saskatoon (CA)

(73) Assignees: The University of Saskatchewan, Saskatoon (CA); National Research Council of Canada, Ottawa (CA)

( * ) Notice: Subject to any disclaimer, the term of this patent is extended or adjusted under 35 U.S.C. 154(b) by 198 days.

This patent is subject to a terminal disclaimer.

(21) Appl. No.: 14/510,232

(22) Filed: Oct. 9, 2014

(65) Prior Publication Data
US 2015/0128301 A1 May 7, 2015

Related U.S. Application Data

(63) Continuation of application No. 13/389,815, filed as application No. PCT/CA2010/001222 on Aug. 4, 2010, now Pat. No. 8,884,100.

(60) Provisional application No. 61/272,057, filed on Aug. 12, 2009, provisional application No. 61/272,117, filed on Aug. 18, 2009.

(51) Int. Cl.
| | |
|---|---|
| C12P 17/06 | (2006.01) |
| C12N 15/82 | (2006.01) |
| C12N 9/10 | (2006.01) |
| C12P 7/22 | (2006.01) |
| C12P 7/42 | (2006.01) |

(52) U.S. Cl.
CPC ....... *C12N 9/1085* (2013.01); *C12N 15/8243* (2013.01); *C12P 7/22* (2013.01); *C12P 7/42* (2013.01); *C12P 17/06* (2013.01); *C12Y 205/01* (2013.01)

(58) Field of Classification Search
None
See application file for complete search history.

(56) References Cited

U.S. PATENT DOCUMENTS 7,112,717 B2 * 9/2006 Valentin ............. C12N 15/8243
435/419

FOREIGN PATENT DOCUMENTS

JP 2000-078979 3/2000
JP 2001-029082 2/2001

OTHER PUBLICATIONS

Sirikantaramas et al, 2005, Plant Cell Physiol., 46:1578-1582.*
van Bakel, 2011, Genome Biology, 12:R102; 1-17.*
Sirikantaramas et al. Tetrahydrocannabinolic Acid Synthase, the Enzyme Controlling Marijuana Psychoactivity, is Secreted into the Storage Cavity of the Glandular Trichomes. Plant Cell Physiol. 46(9): 1578-1582, 2005.
Alvarez JP. et al. Endogenous and synthetic microRNAs stimulate simultaneous, efficient, and localized regulation of multiple targets in diverse species. Plant Cell 18:1134-51.
Bechtold, Nicole et al. In planta Agrobacterium mediated gene transfer by infiltration of adult Arabidopsis thaliana plants. C. R. Acad. Sci. Paries, Sciences de la vie/Life sciences 316:1194-1199. 1993.
Becker D. et al. Fertile transgenic wheat from micropojectile bombardment of scutellar tissue. The Plant Journal (1994) 5(2), 299-307.
Boubakir Z. and Jonathan Page. An aromatic prenyltransferase involved in cannabinoid byosynthesis from Cannabis sative. Banff Conference on Plant Metabolism, Jun. 24 to 28, 2010, Abstract CS6 only.
Collakova, Eva and Dellapenna, Dean. Isolation and Functional Analysis of Homogentisate Phytyltransferase form *Synechocystis* sp. PCC 6803 and Arabidopsis. Plant Physiology, vol. 127, pp. 1113-1124, Nov. 2001.
Datla, Raju et al. Plant promoters for transgene expression. Biotechnology Annual Review. vol. 3, pp. 269-296.
Deblock Marc et al. Transformation of Brassica napus and Brassica oleracea Using Agrobacterium tumefaciens and the Expression of the bar and neo Genes in the Transgenic Plants. Plant Physiol. 91: 694-701, 1989.
Depicker, Ann and Van Montagu, Marc. Post-transcriptional gene silencing in plants. Current Opinion in Cell Biology, 1997, 9: 373-82.
Fellermeier, Monika and Zenk, Meinhart H. Prenylation of olivetolate by a hemp transferase yields cannabigerolic acid, the precursor of tetrahydrocannabinol. FEBS Letters, 1998, 427: 283-285.
Marks M D et al. *Cannabis sativa* (marijuana cultivar Skunk #1) glandular trichomes isolated from female inflorescences *Cannabis sativa* cDNA, mRNA sequence. GenBank Accession GR221141, 2005.
Ohyanagi, H. et al. The Rice Annotation Project Database (RAP-DB): hub for *Oryza sativa* ssp. japonica genome information. GenBank Accession NP_001060083, 2008.
Helliwell, Chris A. Constructs and Methods for Hairpin RNA-Mediated Gene Silencing in Plants. Methods Enzymology 392:24-35. 2005.
Henikoff, Steven et al. TILLING. Traditional Mutagenesis Meets Functional Genomics. Plant Physiology, Jun. 2004, 135:630-6.
Katavic, Vesna et al. In planta transformation of Arabidopsis thaliana. Mol. Gen. Genet., 1994, 245: 363-370.
Katsuyama, Yohei et al. Synthesis of Unnatural Flavonoids and Stilbenes by Exploiting the Plant Biosynthetic Pathway in *Escherichia coli*. Chem Biol., 2007, 14(6) 613-21.
Leonard, Effendi et al. Strain Improvement of Recombinant *Escherichia coli* for Efficient Production of Plant Flavonoids. Molecular Pharmaceutics. [Epub ahead of print] PMID: 18333619 [PubMed-as supplied by publisher]. 2008.

(Continued)

*Primary Examiner* — Jason Deveau Rosen
(74) *Attorney, Agent, or Firm* — Bereskin & Parr LLP; Carmela De Luca (57) ABSTRACT

Nucleic acid molecules from *cannabis* has been isolated and characterized and encode polypeptides having aromatic prenyltransferase activity. Expression or over-expression of the nucleic acids alters levels of cannabinoid compounds. The polypeptides may be used in vivo or in vitro to produce cannabinoid compounds.

22 Claims, 4 Drawing Sheets

(56) References Cited

OTHER PUBLICATIONS

Marks, M. David et al. Identification of candidate genes affecting Δ9-tetrahydrocannabinol biosynthesis in Cannabis sativa. Journal of Experimental Botany, 60(13): 3715-3726. 2009.

Meyer, Peter. Understanding and controlling transgene expression. Trends in Biotechnology. 1995, 13: 332-337.

Moloney, Maurice M. et al. High efficiency transformation of Brassica napus using Agrobacterium vectors. Plant Cell Reports. 1989, 8: 238-242.

Morimoto, Satoshi et al. Purification and Characterization of Cannabichromenic Acid Synthase from Cannabis Sativa. Phytochemistry, 49(6): 1525-1529, 1998.

Nehra, Narender S. et al. Self-fertile transgenic wheat plants regenerated from isolated scutellar tissues following microprojectile bombardment with two distinct gene constructs. The Plant Journal, 1994, 5(2): 285-297.

Page, Jonathan E. Biosynthesisi of Terpenophenolic Metabolites in Hop and Cannabis. Recent Advances in Phytochemistry, 2006, 40: 179-210.

Potrykus, I. Gene Transfer to Plants: Assessment of Published Approaches and Results. Annu. Rev. Plant Physiol. Plant Mol., 1991, 42: 205-225.

Ralston, Lyle. Partial Reconstruction of Flavonoid and Isoflavonoid Biosynthesis in Yeast Using Soybean Type I and Type II Chalcone Isomerases. Plant Physiol. Apr. 2005, 137: 1375-1388.

Rhodes, Carol A. et al. Genetically Transformed Maize Plants from Protoplasts. Science, 1988, 240: 204-207.

Taura, Futoshi et al. Purification and characterization of cannabidiolic-acid synthase from *Cannabis sativa* L. Biochemical analysis of a novel enzyme that catalyzes the oxidocyclization of cannabigerolic acid to cannabidiolic acid. J Biol Chem. 1996, 271: 17411-17416.

Sanford, John C. and Wolf, Edward D. Delivery of substances into cells and tissues using a particle bombardment process. J. Particulate Science and Technology, 1987 5:27-27.

Schwab, Rebecca et al. Highly Specific Gene Silencing by Artificial MicroRNAs in Arabidopsis. The Plant Cell, May 2006 18: 1121-1133.

Shimamoto, K. et al. Fertile transgenic rice plants regenerated from transformed protoplasts. Nature, Mar. 16, 1989, 338: 274-276.

Sirikantaramas, Supaart et al. The gene controlling marijuana psychoactivity: molecular cloning and heterologous expression of Deltal-tetrahydrocannabinolic acid synthase from *Cannabis sativa* L. J Biol Chem. 2004, 279: 39767-39774.

Sonstad, DD et al. Advances in alternative DNA delivery techniques. Plant Cell, Tissueand Organ Culture, 1995 40:1-15.

Stam, Maike et al. Distinct features of post-transcriptional gene silencing by antisense transgenes in single copy and inverted T-DNA repeat loci. Plant J. 2000, 21:27-42.

Taura, Futoshi et al. Cannabidiolic-acid synthase, the chemotype-determining enzyme in the fiber-type Cannabis sativa. FEBS Lett. 2007, 581: 2929-2934.

Taura, Futoshi et al. Characterization of olivetol synthase, a polyketide synthase putatively involved in cannabinoid biosynthetic pathway. FEBS Lett. 2009, 583: 2061-2066.

Vasil, Indra K. Molecular improvement of cereals. Plant Molecular Biology, 1994, 25: 925-937.

Walden, Richard and Wingender, Ruth. Gene-transfer and plant regeneration techniques. Trends in Biotechnology. 1995, 13: 324-331.

Zhang, Haoran et al. Bacterial hosts for natural product production. Mol Pharm. [Epub ahead of print] PMID: 18232637 [PubMed-as supplied by publisher]. 2008.

Shoyama, Y. et al. Biosynthesis of propyl cannabinoid acid and its biosynthetic relationship with pentyl and methyl cannabinoid acids. Phytochemistry. 1984, 23(9): 1909-1912.

Taura, Futoshi et al. T First direct evidence for the mechanism of Δ1-tetrahydrocannabinolic acid biosynthesis. Journal of the American Chemical Society. 1995, 117: 9766-9767.

\* cited by examiner

SEQUENCE LISTING

```
<160> NUMBER OF SEQ ID NOS: 6

<210> SEQ ID NO 1
<211> LENGTH: 1188
<212> TYPE: DNA
<213> ORGANISM: Cannabis sativa

<400> SEQUENCE: 1
atgggactct catcagtttg tacctttca tttcaaacta attaccatac tttattaaat        60
cctcacaata ataatcccaa aacctcatta ttatgttatc gacaccccaa aacaccaatt       120
aaatactctt acaataattt tccctctaaa cattgctcca ccaagagttt tcatctacaa       180
aacaaatgct cagaatcatt atcaatcgca aaaaattcca ttagggcagc tactacaaat       240
caaactgagc ctccagaatc tgataatcat tcagtagcaa ctaaaatttt aaactttggg       300
aaggcatgtt ggaaacttca aagaccatat acaatcatag catttacttc atgcgcttgt       360
ggattgtttg ggaaagagtt gttgcataac acaaatttaa taagttggtc tctgatgttc       420
aaggcattct tttttttggt ggctatatta tgcattgctt cttttacaac taccatcaat       480
cagatttacg atcttcacat tgacagaata aacaagcctg atctaccact agcttcaggg       540
gaaatatcag taaacacagc ttggattatg agcataattg tggcactgtt tggattgata       600
ataactataa aaatgaaggg tggaccactc tatatatttg gctactgttt tggtattttt       660
ggtgggattg tctattctgt tccaccattt agatggaagc aaaatccttc cactgcattt       720
cttctcaatt tcctggccca tattattaca aatttcacat tttattatgc cagcagagca       780
gctcttggcc taccatttga gttgaggcct tcttttactt tcctgctagc atttatgaaa       840
tcaatgggtt cagctttggc tttaatcaaa gatgcttcag acgttgaagg cgacactaaa       900
tttggcatat caaccttggc aagtaaatat ggttccagaa acttgacatt attttgttct       960
ggaattgttc tcctatccta tgtggctgct atacttgctg ggattatctg gccccaggct      1020
ttcaacagta acgtaatgtt actttctcat gcaatcttag cattttggtt aatcctccag      1080
actcgagatt ttgcgttaac aaattacgac ccggaagcag gcagaagatt ttacgagttc      1140
atgtggaagc tttattatgc tgaatattta gtatatgttt tcatataa                   1188

<210> SEQ ID NO 2
<211> LENGTH: 395
<212> TYPE: PRT
<213> ORGANISM: Cannabis sativa

<400> SEQUENCE: 2

Met Gly Leu Ser Ser Val Cys Thr Phe Ser Phe Gln Thr Asn Tyr His
1               5                   10                  15
```

Thr Leu Leu Asn Pro His Asn Asn Pro Lys Thr Ser Leu Leu Cys
                  20                  25                  30

Tyr Arg His Pro Lys Thr Pro Ile Lys Tyr Ser Tyr Asn Asn Phe Pro
             35                  40                  45

Ser Lys His Cys Ser Thr Lys Ser Phe His Leu Gln Asn Lys Cys Ser
 50                  55                  60

Glu Ser Leu Ser Ile Ala Lys Asn Ser Ile Arg Ala Ala Thr Thr Asn
 65                  70                  75                  80

Gln Thr Glu Pro Pro Glu Ser Asp Asn His Ser Val Ala Thr Lys Ile
                 85                  90                  95

Leu Asn Phe Gly Lys Ala Cys Trp Lys Leu Gln Arg Pro Tyr Thr Ile
                100                 105                 110

Ile Ala Phe Thr Ser Cys Ala Cys Gly Leu Phe Gly Lys Glu Leu Leu
                115                 120                 125

His Asn Thr Asn Leu Ile Ser Trp Ser Leu Met Phe Lys Ala Phe Phe
                130                 135                 140

Phe Leu Val Ala Ile Leu Cys Ile Ala Ser Phe Thr Thr Thr Ile Asn
145                 150                 155                 160

Gln Ile Tyr Asp Leu His Ile Asp Arg Ile Asn Lys Pro Asp Leu Pro
                165                 170                 175

Leu Ala Ser Gly Glu Ile Ser Val Asn Thr Ala Trp Ile Met Ser Ile
                180                 185                 190

Ile Val Ala Leu Phe Gly Leu Ile Ile Thr Lys Met Lys Gly Gly
                195                 200                 205

Pro Leu Tyr Ile Phe Gly Tyr Cys Phe Gly Ile Phe Gly Gly Ile Val
                210                 215                 220

Tyr Ser Val Pro Pro Phe Arg Trp Lys Gln Asn Pro Ser Thr Ala Phe
225                 230                 235                 240

Leu Leu Asn Phe Leu Ala His Ile Ile Thr Asn Phe Thr Phe Tyr Tyr
                245                 250                 255

Ala Ser Arg Ala Ala Leu Gly Leu Pro Phe Glu Leu Arg Pro Ser Phe
                260                 265                 270

Thr Phe Leu Leu Ala Phe Met Lys Ser Met Gly Ser Ala Leu Ala Leu
                275                 280                 285

Ile Lys Asp Ala Ser Asp Val Glu Gly Asp Thr Lys Phe Gly Ile Ser
                290                 295                 300

Thr Leu Ala Ser Lys Tyr Gly Ser Arg Asn Leu Thr Leu Phe Cys Ser
305                 310                 315                 320

Gly Ile Val Leu Leu Ser Tyr Val Ala Ala Ile Leu Ala Gly Ile Ile
                325                 330                 335

Trp Pro Gln Ala Phe Asn Ser Asn Val Met Leu Leu Ser His Ala Ile
                340                 345                 350

Leu Ala Phe Trp Leu Ile Leu Gln Thr Arg Asp Phe Ala Leu Thr Asn
                355                 360                 365

Tyr Asp Pro Glu Ala Gly Arg Arg Phe Tyr Glu Phe Met Trp Lys Leu
                370                 375                 380

Tyr Tyr Ala Glu Tyr Leu Val Tyr Val Phe Ile
385                 390                 395

<210> SEQ ID NO 3
<211> LENGTH: 21
<212> TYPE: DNA
<213> ORGANISM: Artificial Sequence
<220> FEATURE:

```
<223> OTHER INFORMATION: Primer

<400> SEQUENCE: 3
gaaggcgaca ctaaatttgg c                                              21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ctggaggatt aaccaaaatg c                                              21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
accaagattg acaggcgttc                                                20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ccttcttctc cacagccttg                                                20
```

AROMATIC PRENYLTRANSFERASE FROM CANNABIS

CROSS-REFERENCE TO RELATED APPLICATIONS

The present application is a continuation of copending U.S. patent application Ser. No. 13/389,815, filed Feb. 10, 2012, which is a National Stage Entry of International Application No. PCT/CA 2010/001222, filed Aug. 4, 2010, which claim priority to U.S. Provisional Patent Applications 61/272,057 filed Aug. 12, 2009 and 61/272,117 filed Aug. 18, 2009, each of these applications being incorporated herein in their entirety by reference.

INCORPORATION OF SEQUENCE LISTING

A computer readable form of the Sequence Listing "P46238US01_SequenceListing.txt" (6,217 bytes), submitted via EFS-WEB and created on Oct. 1, 2014, is herein incorporated by reference.

FIELD OF THE INVENTION

The present invention relates to aromatic prenyltransferase enzyme from *cannabis*, a nucleotide sequence encoding the enzyme and uses of the nucleotide sequence for altering cannabinoid production in organisms.

BACKGROUND OF THE INVENTION

*Cannabis sativa* L. (*cannabis*, hemp, marijuana) is one of the oldest and most versatile domesticated plants, which today finds use as source of medicinal, food, cosmetic and industrial products. It is also well known for its use as an illicit drug owing to its content of psychoactive cannabinoids (e.g. $\Delta^9$-tetrahydrocannabinol, $\Delta^9$-THC). Cannabinoids and other drugs that act through mammalian cannabinoid receptors are being explored for the treatment of diverse conditions such as chronic pain, multiple sclerosis and epilepsy.

Figure 1:
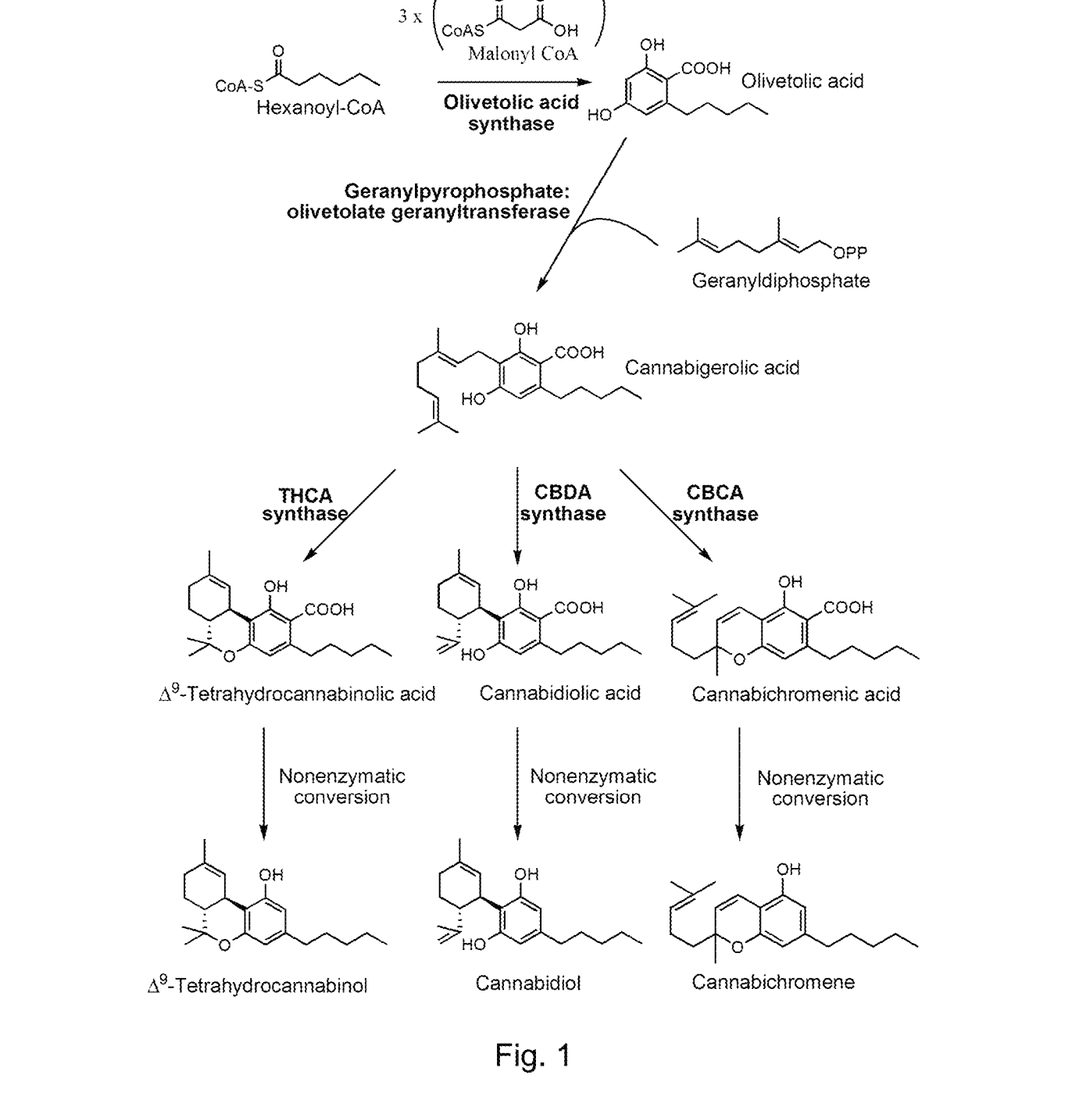
FIG. 1 depicts a proposed pathway leading to the main cannabinoid types in Cannabis sativa showing the central role of geranyl diphosphate:olivetolate geranyl transferase, where THCA synthase is $\Delta^9$-tetrahydrocannabinolic acid synthase, CBDA synthase is cannabidiolic acid synthase, and CBCA synthase is cannabichromenic acid synthase.

Cannabinoids have their biosynthetic origins in both polyketide (phenolic) and terpenoid metabolism and are termed terpenophenolics or prenylated polyketides (Page and Nagel 2006). Cannabinoid biosynthesis occurs primarily in glandular trichomes that cover female flowers at a high density. Cannabinoids are formed by a three-step biosynthetic process: polyketide formation, aromatic prenylation and cyclization (FIG. 1). The only genes known from cannabinoid biosynthesis are the oxidocyclase enzymes that convert cannabigerolic acid to $\Delta^9$-tetrahydrocannabinolic acid (THCA) or cannabidiolic acid (CBDA) (Sirikantaramas et al. 2005, Taura et al. 2007).

The first enzymatic step in cannabinoid biosynthesis is the formation of olivetolic acid by a putative polyketide synthase enzyme, termed olivetolic acid synthase. A polyketide synthase from *cannabis* has recently been shown to form olivetol but not olivetolic acid (Taura et al. 2009). The second enzymatic step in cannabinoid biosynthesis is the prenylation of olivetolic acid to form cannabigerolic acid (CBGA) by the enzyme geranylpyrophosphate:olivetolate geranyltransferase. It is this enzyme which we describe in this Report. Using crude protein extracts of *cannabis* leaves, Fellermeier and Zenk (1998) identified an enzyme that catalyzed the prenylation of olivetolic acid with geranyl diphosphate. CBGA is a central branch-point intermediate for the biosynthesis of the different major classes of cannabinoids. Alternative cyclization of the prenyl side-chain of CBGA yields THCA or its isomers CBDA or cannabichromenic acid (CBCA) (FIG. 1). Pioneering work by the Shoyama group led to the identification and purification of the three enzymes responsible for these cyclizations (Morimoto et al. 1998, Taura et al. 1996, Taura et al. 1995). Subsequent cloning of THCA synthase showed it to be an oxidoreductase that catalyzes the oxidative cyclization of CBGA to form THCA (Sirikantaramas et al. 2004). The genes for THCA synthase and CBDA synthase have been reported in Japan (Japanese Patent Publication 2000-078979; Japanese Patent Publication 2001-029082).

Cannabinoids are valuable plant-derived natural products. Genes encoding enzymes of cannabinoid biosynthesis will be useful in metabolic engineering of *cannabis* varieties that contain ultra low levels of THC and other cannabinoids. Such genes may also prove useful for creation of specific *cannabis* varieties for the production of cannabinoid-based pharmaceuticals, or for reconstituting cannabinoid biosynthesis in other organisms such as bacteria or yeast.

There remains a need in the art to identify aromatic prenyltransferase enzymes, and nucleotide sequences encoding such enzymes, that catalyze the transfer of prenyl groups.

SUMMARY OF THE INVENTION

In a first aspect of the invention, there is provided an isolated or purified nucleic acid molecule comprising a nucleotide sequence having at least 85% sequence identity to SEQ ID NO: 1.

In a second aspect of the invention, there is provided an isolated or purified polypeptide comprising an amino acid sequence having at least 85% sequence identity to SEQ ID NO: 2.

In a third aspect of the invention, there is provided a process of transferring a prenyl group comprising: reacting a prenyl group acceptor molecule with a prenyl group donor molecule in presence of an aromatic prenyltransferase of the present invention, thereby transferring the prenyl group from the prenyl group donor molecule to the prenyl group acceptor molecule.

In a fourth aspect of the invention, there is provided a method of altering levels of cannabinoid compounds in an organism, cell or tissue comprising expressing or over-expressing a nucleic acid molecule of the present invention in the organism, cell or tissue.

In a fifth aspect of the present invention, there is provided a method of altering levels of cannabinoid compounds in an organism, cell or tissue comprising using a nucleic acid molecule of the present invention, or a part thereof, to silence an aromatic prenyltransferase gene in the organism, cell or tissue.

Aromatic prenyltransferase enzymes, and nucleotide sequences encoding such enzymes, have now been identified and characterized. The nucleotide sequence may be used to create, through breeding, selection or genetic engineering, *cannabis* plants that overproduce or under-produce cannabinoid compounds or mixtures thereof. This prenyltransferase nucleotide sequence may also be used, alone or in combination with genes encoding other steps in cannabinoid synthesis pathways, to engineer cannabinoid biosynthesis in other plants or in microorganisms (e.g. yeast, bacteria, fungi) or other prokaryotic or eukaryotic organisms. In addition, knocking out this gene in *cannabis* could be used to block cannabinoid biosynthesis and thereby reduce production of cannabinoids. The aromatic prenyltransferase may also be useful as a biocatalytic tool for prenylation of small molecules.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Some embodiments of the present invention relate to an isolated or purified nucleic acid molecule having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 1.

Further included are nucleic acid molecules that hybridize to the above disclosed sequences. Hybridization conditions may be stringent in that hybridization will occur if there is at least a 90%, 95% or 97% sequence identity with the nucleic acid molecule that encodes the enzyme of the present invention. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001).

As will be appreciated by the skilled practitioner, slight changes in nucleic acid sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (e.g., anti-sense, co suppression, or RNAi), partial sequences often work as effectively as full length versions. The ways in which the nucleotide sequence can be varied or shortened are well known to persons skilled in the art, as are ways of testing the effectiveness of the altered genes. In certain embodiments, effectiveness may easily be tested by, for example, conventional gas chromatography. All such variations of the genes are therefore included as part of the present disclosure.

As will be appreciated by one of skill in the art, the length of the nucleic acid molecule described above will depend on the intended use. For example, if the intended use is as a primer or probe for example for PCR amplification or for screening a library, the length of the nucleic acid molecule will be less than the full length sequence, for example, 15-50 nucleotides. In these embodiments, the primers or probes may be substantially identical to a highly conserved region of the nucleic acid sequence or may be substantially identical to either the 5' or 3' end of the DNA sequence. In some cases, these primers or probes may use universal bases in some positions so as to be 'substantially identical' but still provide flexibility in sequence recognition. It is of note that suitable primer and probe hybridization conditions are well known in the art.

Some embodiments relate to an isolated or purified polypeptide having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence as set forth in SEQ ID NO: 2.

Some embodiments relate to a vector, construct or expression system containing an isolated or purified polynucleotide having at least 85% sequence identity to SEQ ID NO: 1. Accordingly, there is provided a method for preparing a vector, construct or expression system including such a sequence, or a part thereof, for introduction of the sequence or partial sequence in a sense or anti-sense orientation, or a complement thereof, into a cell.

In some embodiments, the isolated and/or purified nucleic acid molecules, or vectors, constructs or expression systems comprising these isolated and/or purified nucleic acid molecules, may be used to create transgenic organisms or cells of organisms that produce polypeptides with aromatic prenyltransferase activity. Therefore, one embodiment relates to transgenic organisms, cells or germ tissues of the organism including an isolated and/or purified nucleic acid molecule having at least 85% sequence identity to SEQ ID NO: 1.

Preferably, the organism is a plant, microorganism or insect. Plants are preferably of the genus *Cannabis*, for example *Cannabis sativa* L., *Cannabis indica* Lam. and *Cannabis ruderalis* Janisch, especially *Cannabis sativa*. Microorganisms are preferably bacteria (e.g. *Escherichia coli*) or yeast (e.g. *Saccharomyces cerevisiae*). Insect is preferably *Spodoptera frugiperda*.

Organisms, cells and germ tissues of this embodiment may have altered levels of cannabinoid compounds. With reference to FIG. 1, it will be appreciated by one skilled in the art that expression or over-expression of the nucleic acid molecule will result in expression or over-expression of the aromatic prenyltransferase enzyme which may result in increased production of cannabinoid compounds such as cannabigerolic acid, $\Delta^9$-tetrahydrocannabinolic acid, cannabidiolic acid, cannabichromenic acid, $\Delta^9$-tetrahydrocannabinol, cannabidiol, cannabichromene, etc. Silencing of aromatic prenyltransferase in the organism, cell or tissue will result in under-expression of the aromatic prenyltransferase which may result in accumulation of precursors to the aforementioned compounds.

Expression or over-expression of the nucleic acid molecule may be done in combination with expression or over-expression of one or more other nucleic acids that encode one or more enzymes in a cannabinoid biosynthetic pathway. Some examples of other nucleic acids include: nucleic acids that encode an olivetolic acid synthase, a THCA synthase, a CBDA synthase and/or a CBCA synthase.

Expression or over-expression of the aromatic prenyltransferase enzyme of the present invention compared to a control which has normal levels of the enzyme for the same variety grown under similar or identical conditions will result in increased levels of cannabinoid compounds, for example, 1-20%, 2-20%, 5-20%, 10-20%, 15-20%, 1-15%, 1-10%, 2-15%, 2-10%, 5-15%, or 10-15% (w/w).

Transfer of a prenyl group from a prenyl group donor molecule to a prenyl group acceptor molecule in the presence of an aromatic prenyltransferase of the present invention may be accomplished in vivo or in vitro. As previously mentioned, such transfers in vivo may be accomplished by expressing or over-expressing the nucleic acid molecule in an organism, cell or tissue. The organism, cell or tissue may naturally contain the prenyl group acceptor molecule and/or the prenyl group donor molecule, or the prenyl group receptor molecule and/or prenyl group donor molecule may be provided to the organism, cell or tissue for uptake and subsequent reaction.

In vitro, the prenyl group acceptor molecule, prenyl group donor molecule and aromatic prenyltransferase may be mixed together in a suitable reaction vessel to effect the reaction. In vitro, the aromatic prenyltransferase may be used in combination with other enzymes to effect a complete synthesis of a target compound from a precursor. For example, such other enzymes may be implicated in a cannabinoid biosynthetic pathway as described in FIG. 1.

Terms:

In order to facilitate review of the various embodiments of the disclosure, the following explanations of specific terms are provided:

Codon degeneracy: It will be appreciated that this disclosure embraces the degeneracy of codon usage as would be understood by one of ordinary skill in the art and as illustrated in Table 1.

TABLE 1

| Codon Degeneracies | |
|---|---|
| Amino Acid | Codons |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Conservative substitutions: Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. Table 2 provides an exemplary list of conservative substitutions.

TABLE 2

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |

TABLE 2-continued

Conservative Substitutions

| Type of Amino Acid | Substitutable Amino Acids |
|---|---|
| Aliphatic | Val, Ile, Leu, Met |
| Basic | Lys, Arg, His |
| Aromatic | Phe, Tyr, Trp |

Complementary nucleotide sequence: "Complementary nucleotide sequence" of a sequence is understood as meaning any nucleic acid molecule whose nucleotides are complementary to those of sequence of the disclosure, and whose orientation is reversed (antiparallel sequence).

Degree or percentage of sequence homology: The term "degree or percentage of sequence homology" refers to degree or percentage of sequence identity between two sequences after optimal alignment. Percentage of sequence identity (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide sequences at random and over the whole of their length. Sequence identity can be determined, for example, by computer programs designed to perform single and multiple sequence alignments. It will be appreciated that this disclosure embraces the degeneracy of codon usage as would be understood by one of ordinary skill in the art. Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins.

Increasing, decreasing, modulating, altering or the like: As will be appreciated by one of skill in the art, such terms refers to comparison to a similar variety grown under similar conditions but without the modification resulting in the increase, decrease, modulation or alteration. In some cases, this may be an untransformed control, a mock transformed control, or a vector-transformed control.

Isolated: As will be appreciated by one of skill in the art, "isolated" refers to polypeptides or nucleic acids that have been "isolated" from their native environment.

Nucleotide, polynucleotide, or nucleic acid sequence: "Nucleotide, polynucleotide, or nucleic acid sequence" will be understood as meaning both double-stranded or single-stranded in the monomeric and dimeric (so-called in tandem) forms and the transcription products thereof.

Sequence identity: Two amino-acids or nucleotidic sequences are said to be "identical" if the sequence of amino-acids or nucleotidic residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2: 482 (1981), by the homology alignment algorithm of Needleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BEST-FIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary nucleic acid molecules. Homologs of the CsPT1 genes described herein obtained from other organisms, for example plants, may be obtained by screening appropriate libraries that include the homologs, wherein the screening is performed with the nucleotide sequence of the specific CsPT1 genes disclosed herein, or portions or probes thereof, or identified by sequence homology search using sequence alignment search programs such as BLAST, FASTA.

Methods:

Nucleic acid isolation and cloning is well established. Similarly, an isolated gene may be inserted into a vector and transformed into a cell by conventional techniques. Nucleic acid molecules may be transformed into an organism. As known in the art, there are a number of ways by which genes, vectors, constructs and expression systems can be introduced into organisms, and a combination of transformation and tissue culture techniques have been successfully integrated into effective strategies for creating transgenic organisms. These methods, which can be used in the invention, have been described elsewhere (Potrykus, 1991; Vasil, 1994; Walden and Wingender, 1995; Songstad et al., 1995), and are well known to persons skilled in the art. Suitable vectors are well known to those skilled in the art and are described in general technical references such as Pouwels et al., (1986).

Particularly suitable vectors include the Ti plasmid vectors. For example, one skilled in the art will certainly be aware that, in addition to *Agrobacterium* mediated transformation of *Arabidopsis* by vacuum infiltration (Bechtold, et al., 1993) or wound inoculation (Katavic et al., 1994), it is equally possible to transform other plant species, using *Agrobacterium* Ti-plasmid mediated transformation (e.g., hypocotyl (DeBlock et al., 1989) or cotyledonary petiole (Moloney et al., 1989) wound infection), particle bombardment/biolistic methods (Sanford et al., 1987; Nehra. et al., 1994; Becker et al., 1994) or polyethylene glycol-assisted, protoplast transformation (Rhodes et al., 1988; Shimamoto et al., 1989) methods.

As will also be apparent to persons skilled in the art, and as described elsewhere (Meyer, 1995; Datla et al., 1997), it is possible to utilize promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use herein may be inducible, constitutive, or tissue-specific or have various combinations of such characteristics. Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). It may be desirable to use a tissue-specific or developmentally regulated promoter instead of a constitutive promoter in certain circumstances. A tissue-specific promoter allows for overexpression in certain tissues without affecting expression in other tissues.

The promoter and termination regulatory regions will be functional in the host cell and may be heterologous (that is, not naturally occurring) or homologous (derived from the plant host species) to the cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via *Agrobacterium* and screening for altered cannabinoid levels.

The nucleic acid molecule or fragments thereof may be used to block cannabinoid biosynthesis in organisms that naturally produce cannabinoid compounds. Silencing using a nucleic acid molecule of the present invention may be accomplished in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell and Waterhouse, 2005). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab et al, 2006; Alvarez et al, 2006). In this method, 21 nucleotide long fragments of the gene to be silenced are introduced into a pre-miRNA gene to form a pre-amiRNA construct. The pre-miRNA construct is transferred into the organism genome using transformation methods apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam et al., 2000.

Sense co-suppression techniques involve introducing a highly expressed sense transgene into a plant resulting in reduced expression of both the transgene and the endogenous gene (Depicker et al., 1997). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in an organism (Henikoff, et al., 2004; Li et al., 2001). TILLING involves treating germplasm or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from organisms in the mutagenized population. Amplified mutant genes may be annealed to wild-type genes to find mismatches between the mutant genes and wild-type genes. Detected differences may be traced back to the organism which had the mutant gene thereby revealing which mutagenized organism will have the desired expression (e.g. silencing of the gene of interest). These organisms may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in organism genomes that can also be detected using PCR in a manner similar to TILLING.

EXAMPLES

Example 1: Isolation and Characterization of CsPT1 Gene and Enzyme

An Expressed Sequence Tag (EST) catalog (9157 ESTs consisting of 4110 unigenes) obtained by sequencing cDNAs from a *cannabis* trichome-specific cDNA library was analyzed for the presence of prenyltransferase-like proteins. One unigene of 20 members showed similarity to homogentisate phytyltransferase VTE2-2, a prenyltransferase that catalyzes the prenylation of homogentisic acid with phytyldiphosphate in tocopherol biosynthesis (Collakova and DellaPenna, 2001). This prenyltransferase was named CsPT1 (*Cannabis sativa* prenyltransferase 1). The open reading frame (ORF) of CsPT1 including the terminal stop codon TAA, and the corresponding amino acid sequence encoded by the ORF are given below as SEQ ID NO: 1 and SEQ ID NO: 2.

```
Cannabis sativa CsPT1-1188 bp
                                    (SEQ ID NO: 1)
ATGGGACTCTCATCAGTTTGTACCTTTTCATTTCAAACTAATTACCATA
CTTTATTAAATCCTCACAATAATAATCCCAAAACCTCATTATTATGTTA
TCGACACCCCAAAACACCAATTAAATACTCTTACAATAATTTTCCCTCT
AAACATTGCTCCACCAAGAGTTTTCATCTACAAAACAAATGCTCAGAAT
CATTATCAATCGCAAAAAATTCCATTAGGGCAGCTACTACAAATCAAAC
TGAGCCTCCAGAATCTGATAATCATTCAGTAGCAACTAAAATTTTAAAC
TTTGGGAAGGCATGTTGGAAACTTCAAAGACCATATACAATCATAGCAT
TTACTTCATGCGCTTGTGGATTGTTTGGGAAAGAGTTGTTGCATAACAC
AAATTTAATAAGTTGGTCTCTGATGTTCAAGGCATTCTTTTTTTTGGTG
GCTATATTATGCATTGCTTCTTTTACAACTACCATCAATCAGATTTACG
ATCTTCACATTGACAGAATAAACAAGCCTGATCTACCACTAGCTTCAGG
```

```
-continued
GGAAATATCAGTAAACACAGCTGGATTATGAGCATAATTGTGGCACTG
TTTGGATTGATAATAACTATAAAAATGAAGGGTGGACCACTCTATATAT
TTGGCTACTGTTTTGGTATTTTTGGTGGGATTGTCTATTCTGTTCCACC
ATTTAGATGGAAGCAAAATCCTTCCACTGCATTTCTTCTCAATTTCCTG
GCCCATATTATTACAAATTTCACATTTTATTATGCCAGCAGAGCAGCTC
TTGGCCTACCATTTGAGTTGAGGCCTTCTTTTACTTTCCTGCTAGCATT
TATGAAATCAATGGGTTCAGCTTTGGCTTTAATCAAAGATGCTTCAGAC
GTTGAAGGCGACACTAAATTTGGCATATCAACCTTGGCAAGTAAATATG
GTTCCAGAAACTTGACATTATTTTGTTCTGGAATTGTTCTCCTATCCTA
TGTGGCTGCTATACTTGCTGGGATTATCTGGCCCCAGGCTTTCAACAGT
AACGTAATGTTACTTTCTCATGCAATCTTAGCATTTTGGTTAATCCTCC
AGACTCGAGATTTTGCGTTAACAAATTACGACCCGGAAGCAGGCAGAAG
ATTTTACGAGTTCATGTGGAAGCTTTATTATGCTGAATATTTAGTATAT
GTTTTCATATAA
```

```
Cannabis sativa CsPT1-395 aa
                                    (SEQ ID NO: 2)
MGLSSVCTFSFQTNYHTLLNPHNNNPKTSLLCYRHPKTPIKYSYNNFPS
KHCSTKSFHLQNKCSESLSIAKNSIRAATTNQTEPPESDNHSVATKILN
FGKACWKLQRPYTIIAFTSCACGLFGKELLHNTNLISWSLMFKAFFFLV
AILCIASFTTTINQIYDLHIDRINKPDLPLASGEISVNTAWIMSIIVAL
FGLIITIKMKGGPLYIFGYCFGIFGGIVYSVPPFRWKQNPSTAPLLNFL
AHIITNFTFYYASRAALGLPFELRPSFTFLLAFMKSMGSALALIKDASD
VEGDTKFGISTLASKYGSRNLTLFCSGIVLLSYVAAILAGIIWPQAFNS
NVMLLSHAILAFWLILQTRDFALTNYDPEAGRRFYEFMWKLYYAEYLVY
VFI
```

Example 2: Expression of Recombinant CsPT1 in Sf9 and Yeast Cells

For expression in insect cells, the open reading frame of CsPT1 was cloned into pENTR/D-TOPO (Invitrogen), recombined into pDEST10 (Invitrogen) and transformed into *E. coli* DH10Bac (Invitrogen). All cloning procedures were verified by sequencing. Bacmid DNA was isolated and transfected into Sf9 insect cells to generate recombinant baculovirus. The primary viral stock was amplified four times to produce a titer viral stock (P4) that was used to infect Sf9 insect cell cultures for protein expression. Expression cultures were grown in SF-900 II SFM medium (Invitrogen), either as adherent cultures (15 ml) in T-75 flasks or as suspension cultures (200 ml) in 500 ml spinner flasks. Expression cultures ($1.5 \times 10^6$ cells/ml) were infected with P4 viral stock at a multiplicity of infection of 5 and grown for 72 h at 28° C. before harvesting. Insect cell microsomes were isolated by centrifuging the cells at 500 rpm for 10 min at 4° C., decanting the supernatant and then washing the pellet twice with PBS buffer. The pellets were washed twice with buffer A (50 mM HEPES pH 7.5, 0.5 mM EDTA, 0.1 mM DTT and 10% glycerol) and then resuspended in buffer A. The cell suspension was sonicated for 1 min to lyse the cells. The lysed cells were centrifuged at 10,000 rpm for 20 min at 4° C. and 14,000 rpm for 30 min at 4° C. to remove cell debris. The microsomes were collected by centrifugation at 100,000×g for 90 min at 4° C. The microsomal pellet was resuspended in 200 µl storage buffer (50 mM HEPES pH 7.5, 1 mM DTT and 10% glycerol) and stored at −20° C.

For expression in yeast (*Saccharomyces cerevisiae*), the open reading frame CsPT1 was cloned into yeast expression vector pESC-TRP (Stratagene) at Spe1 (5') and Cla1 (3') sites. The sequence of resulting plasmid pESC-CsPT1 was used to transform *S. cerevisiae* INVSc1 (Invitrogen), which was selected by SD (lacking tryptophan) medium by the lithium acetate method. For the expression of recombinant protein, the transformed yeast was pre-cultured in 10 ml of SG (-tryptophan) medium (yeast nitrogen base without amino acids, yeast synthetic drop-out medium without tryptophan, 2% galactose) at 30° C. for overnight. The pre-cultured yeast suspension was inoculated into 200 ml of fresh medium (yeast nitrogen base without amino acids, yeast synthetic drop-out medium without tryptophan, 2% galactose) and grown for 48 h at 30° C. Yeast microsomes were isolated by centrifuging the cells at 3500 rpm for 5 min at 4° C., decanting the supernatant and then washing the pellet with wash buffer (20 mM Tris-HCl pH 7.5, 0.5 mM EDTA, 0.1 M KCl). The pellets were re-suspended in 20 mM Tris-HCl buffer (pH 7.5) containing 0.5 mM EDTA, 0.6 M sorbitol and 1 mM phenylmethylsulfonyl fluoride. The cell suspension was shaken with glass beads (0.5 mm) in mini bead beater to lyse the cells. The lysed cells were centrifuged at 10,000 rpm for 20 min at 4° C. and 14,000 rpm for 30 min at 4° C. to remove cell debris. The microsomes were collected by centrifugation at 100,000×g for 90 min at 4° C. The microsomal pellet was re-suspended in 50 µl storage buffer (20 mM Tris-HCl pH 7.5, 0.5 mM EDTA, 0.6 M sorbitol and 20% glycerol) and stored at −20° C.

Example 3: Biochemical Activity of CsPT1 Enzyme

The prenyltransferase assay for CsPT1 comprised 100 mM Tris-HCl (pH 7.5), 0.2 mM olivetolic acid, 1 mM geranyl diphosphate and 5 mM $MgCl_2$ in a final volume 100 µl. The reaction was initiated by addition of a 5 µl aliquot of microsomal preparation (64 µg protein), either from insect cells or yeast. After incubation for 1 h at 37° C., the reaction was terminated by addition of 10 µl 6 N HCl and extracted twice with 200 µl of ethyl acetate. The organic phase was evaporated to dryness and the residue dissolved in 50 µl of methanol. A 20 µl aliquot was analyzed by HPLC using a Waters 2695 system equipped with photodiode array detector on a Sunfire C18 reversed phase column 3.5 µm (4.6×150 mm) at a column temperature of 30° C. The mobile phase at 1 ml/min consisted of 50% water (containing 0.1% trifluoroacetic acid [TFA] [v/v]) and 50% acetonitrile over 10 min, 50% to 100% acetonitrile over 10 min, 100% acetonitrile to 50% acetonitrile over 1 min, 50% acetonitrile and 50% water over 4 min. The products were detected at 270 nm with photodiode array detection.

Figure 2:
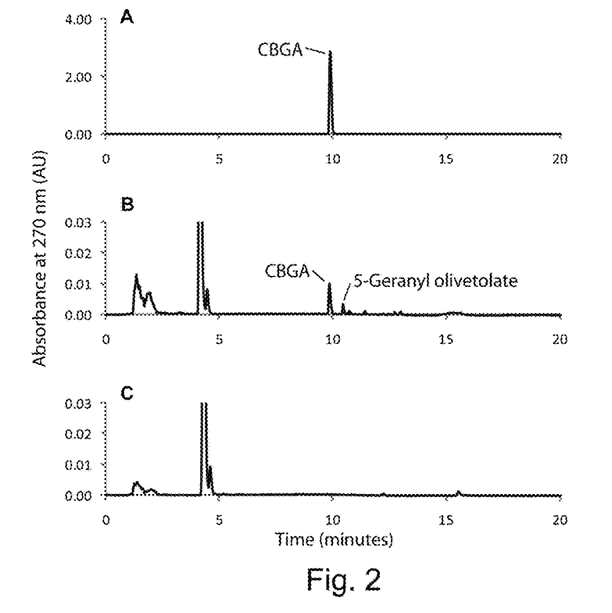
FIG. 2 depicts HPLC analysis of the enzymatic activity of aromatic prenyltransferase CsPT1 expressed in Sf9 insect cells with olivetolic acid and geranyl diphosphate (GPP). (A) Chromatogram of authentic cannabigerolic acid standard (9.9 min). (B) Chromatogram showing reaction products obtained by incubation of insect cell microsomes containing recombinant CsPT1 with olivetolic acid, geranyl diphosphate and $MgCl_2$. The cannabigerolic acid (9.9 min) and 5-geranyl olivetolic acid (10.5 min) peaks are indicated. Olivetolic acid elutes at 4.3 min. (C) Chromatogram showing reaction products obtained by incubation of insect cell microsomes containing recombinant CsPT1 with olivetolic acid and $MgCl_2$ in the absence of geranyl diphosphate. All chromatograms were extracted at 270 nm.
Figure 3:
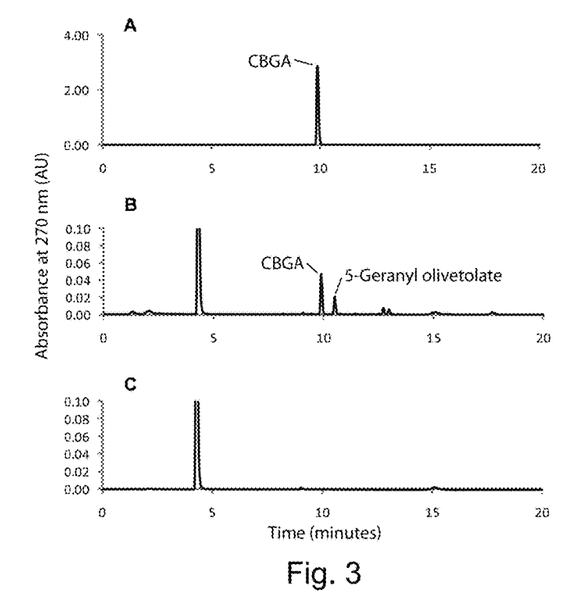
FIG. 3 depicts HPLC analysis of the enzymatic activity of aromatic prenyltransferase CsPT1 expressed in yeast with olivetolic acid and geranyl diphosphate (GPP). (A) Chromatogram of authentic cannabigerolic acid standard (9.9 min). (B) Chromatogram showing reaction products obtained by incubation of yeast microsomes containing recombinant CsPT1 with olivetolic acid, geranyl diphosphate and $MgCl_2$. The cannabigerolic acid (9.9 min) and 5-geranyl olivetolic acid (10.5 min) peaks are indicated. (C) Chromatogram showing reaction products obtained by incubation of yeast microsomes containing recombinant CsPT1 with olivetolic acid and $MgCl_2$ in the absence of geranyl diphosphate. All chromatograms were extracted at 270 nm.
Figure 4:
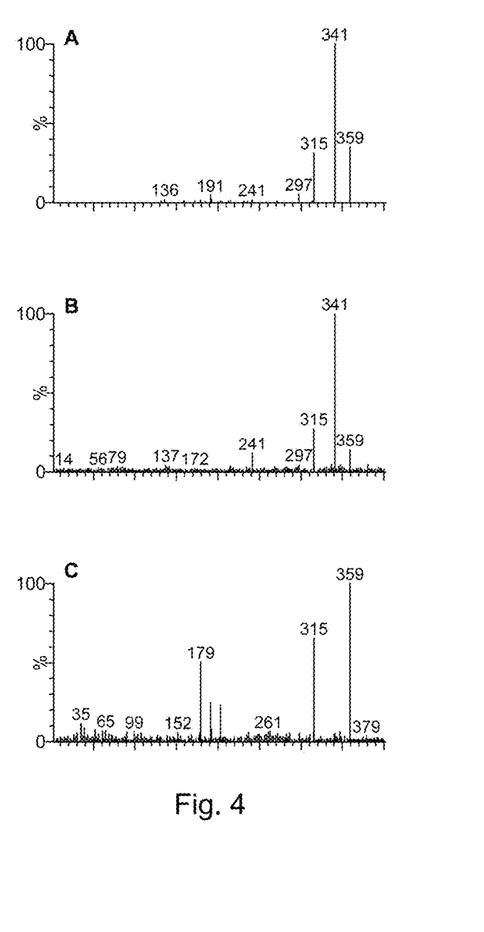
FIG. 4 depicts LC-MS analysis of enzymatic products formed by insect cell microsomes containing recombinant CsPT1 from olivetolic acid and geranyl diphosphate. Mass spectrometry was performed using electrospray ionization in negative mode. (A) Mass spectrum of cannabigerolic acid standard. (B) Mass spectrum of cannabigerolic acid peak (retention time 9.9 min) produced geranylation of olivetolic acid by CsPT1 showing the same ionization pattern as the cannabigerolic acid standard. (C) Mass spectrum of 5-geranyl olivetolic acid peak (retention time 10.5 min) produced by geranylation of olivetolic acid by CsPT1.
Figure 5:
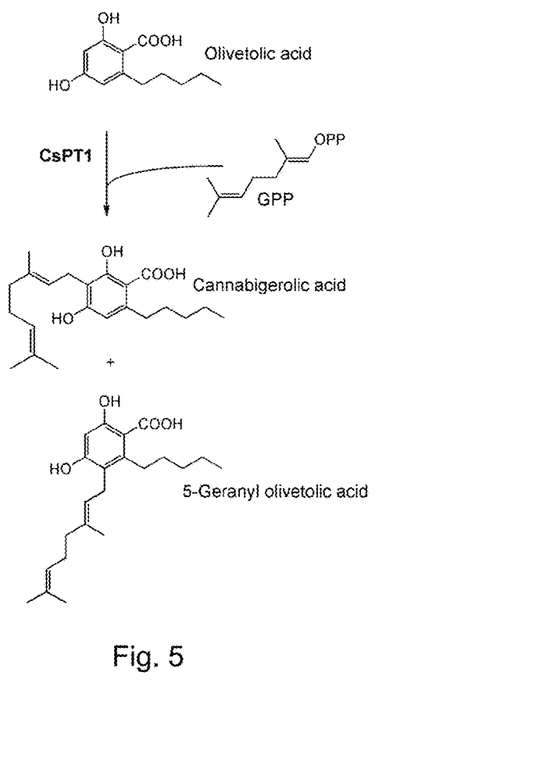
FIG. 5 depicts prenylation reactions catalyzed by recombinant CsPT1. Two products, cannabigerolic acid and 5-geranyl olivetolic acid, are formed by geranylation of olivetolic acid.

CsPT1 expressed in Sf9 insect cells and yeast was assayed with olivetolic acid and was found to catalyze the transfer of the C10 prenyl group of geranyl diphosphate to form two products: the major product cannabigerolic acid (or 3-geranyl olivetolate) eluting at 9.9 min and the minor product 5-geranyl olivetolate eluting at 10.5 min (FIGS. 2 and 3). Cannabigerolic acid was identified by comparison of retention time and LC-MS analysis in comparison to an authentic cannabigerolic acid standard; 5-geranyl olivetolate was identified by LC-MS analysis (FIG. 4). Therefore CsPT1 is an enzyme that functions as a geranylpyrophosphate:olivetolate geranyltransferase that forms both cannabigerolic acid and 5-geranyl olivetolic acid (FIG. 5).

Figure 6:
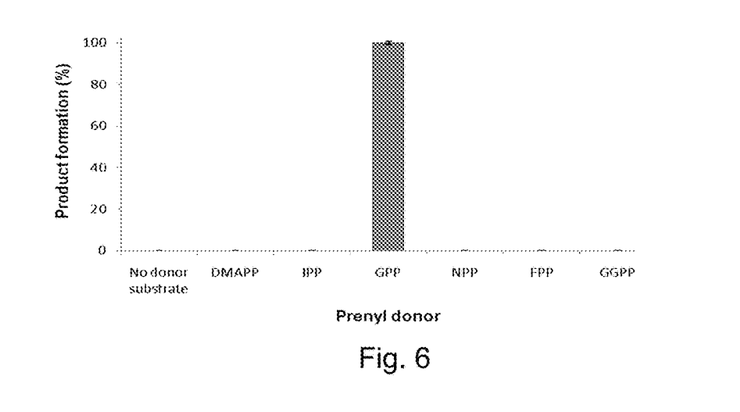
FIG. 6 depicts use of different prenyl diphosphate donor substrates by recombinant CsPT1, where DMAPP is dimethylally diphosphate, IPP is isopenetnyl diphosphate, GPP is geranyl diphosphate, NPP is neryl diphosphate, FPP is farnesyl diphosphate, and GGPP is geranylgeranyl diphosphate. Bar represents mean+/− standard deviation (n=3).

The activity of the recombinant CsPT1 was assayed to determine its use of different prenyl diphosphate donor substrates. As shown in FIG. 6, the enzyme only used geranyl diphosphate (GPP) as a prenyl donor.

The activity of the recombinant CsPT1 was assayed to determine its use of different aromatic acceptor substrates using geranyl diphosphate as the prenyl donor substrate. Table 3 shows that CsPT1 geranylated olivetolic acid as well as olivetol, phlorisovalerophenone, naringenin and resveratrol. In Table 3, Product yield is the yield of prenylated products as measured by HPLC peak area with the yield of cannabigerolic acid and 5-geranyl olivetolic acid set to 100%. Phlorisovalerophenone has not been detected in cannabis. It has been shown that cannabinoids with short side-chains exist in cannabis (e.g. tetrahydrocannabivarinic acid having a propyl side-chain instead of the pentyl side-chain of THC acid (Shoyama 1984). Given that CsPT1 accepts a variety of aromatic acceptor substrates, this enzyme likely is able to prenylate analogs of olivetolic acid that have differing side-chain length.

TABLE 3

Substrate specificity of CsPT1 with various aromatic substrates

| Substrate | Product yield (%) |
| --- | --- |
| Olivetolic acid | 100 |
| Olivetol | 30 |
| Hexanoyl triacetic acid lactone | 0 |
| Homogentisic acid | 0 |
| Phloroglucinol | 0 |
| Phlorisovalerophenone | 250 |
| Resveratrol | 32 |
| Naringenin | 31 |
| Chalconaringenin | 0 |
| Chrysoeriol | 0 |
| Luteolin | 0 |

Figure 7:
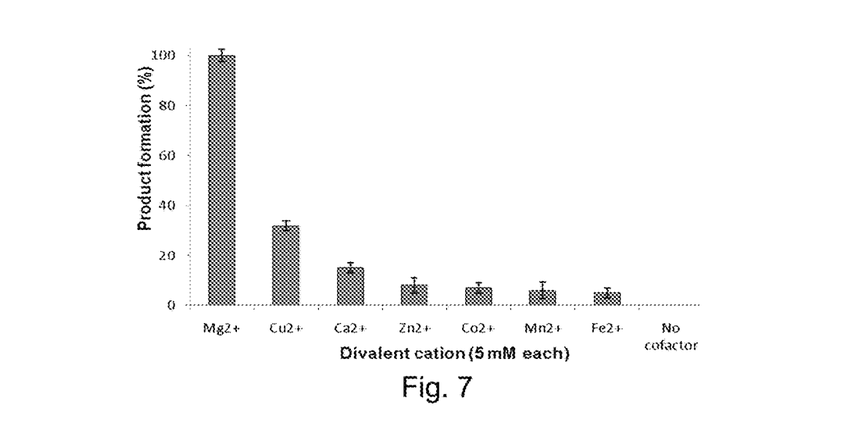
FIG. 7 depicts use of different divalent cations by recombinant CsPT1. CsPT1 was tested with olivetolic acid, geranyl diphosphate and the different divalent cations at 5 mM each. Bars represent mean+/− standard deviation (n=3).

Recombinant CsPT1 was tested for its preference for different divalent cations which are required for prenyltransferase activity. FIG. 7 shows that CsPT1 gave the highest yield of CBGA in the presence of $Mg^{2+}$.

The catalytic properties of recombinant CsPT1 were tested to determine the kinetics of geranylation of olivetolic acid. The $K_m$ for olivetolic acid was 60 mM, the $K_m$ for geranyl diphosphate was 150 mM, and the $K_m$ for $Mg^{2+}$ was 3 mM.

Example 4: Expression of CsPT1 Gene in Cannabis Plants

Figure 8:
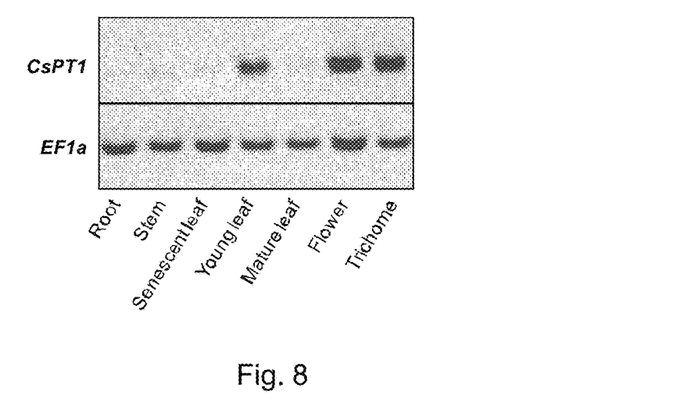
FIG. 8 depicts RT-PCR analysis of the expression of CsPT1 in different cannabis organs. First-strand cDNA reverse transcribed from total RNA was used as PCR template. Gene-specific primers for amplification of CsPT1 elongation factor 1 alpha (ELFa) were used for standard PCR. Amplification products were analyzed on a 1% agarose gel.

To examine the expression of CsPT1 transcript in cannabis plants, total RNA was isolated using a combination of CTAB and RNeasy (Qiagen) from different cannabis organs and used as a template for first-strand cDNA synthesis. Gene-specific primer pairs were used to amplify a 195 bp fragment of CsPT1 (5'-GAA GGC GAC ACT AAA TTT GGC-3' (SEQ ID NO: 3) and 5'-CTG GAG GAT TAA CCA AAA TGC-3' (SEQ ID NO: 4)) and a 205 bp fragment of EF1alpha (5'-ACC AAG ATT GAC AGG CGT TC-3' (SEQ ID NO: 5) and 5'-CCT TCT TCT CCA CAG CCT TG-3' (SEQ ID NO: 6)). The PCR amplification was performed for 25 cycles with denaturation at 94° C. for 30 sec, annealing at 60° C. for 45 sec and elongation at 72° C. for 60 sec, followed by 72° C. for 5 min. The amplification products were analyzed on a 1% gel visualized using GelRed™ and ultraviolet light. As shown in FIG. 8, CsPT1 was expressed mainly in young leaves, female flowers and glandular trichomes isolated from female flowers.

The present gene encodes a geranylpyrophosphate:olivetolate geranyltransferase enzyme from cannabis. This gene could be used to create, through breeding, targeted mutagenesis or genetic engineering, cannabis plants with enhanced cannabinoid production. In addition, inactivating or silencing this gene in cannabis could be used to block cannabinoid biosynthesis and thereby reduce production of cannabinoids such as THCA, the precursor of THC, in cannabis plants (e.g. industrial hemp). This gene could be used, in combination with genes encoding other enzymes in the cannabinoid pathway, to engineer cannabinoid biosynthesis in other plants or in microorganisms.

REFERENCES

The contents of the entirety of each of which are incorporated by this reference.

Alvarez J P, Pekker I, Goldshmidt A, Blum E, Amsellem Z, Eshed Y (2006) Endogenous and synthetic microRNAs stimulate simultaneous, efficient, and localized regulation of multiple targets in diverse species. *Plant Cell* 18:1134-51.

Bechtold N, Ellis J, Pelletier G (1993) In planta *Agrobacterium*-mediated gene transfer by infiltration of adult *Arabidopsis thaliana* plants. *C R Acad Sci Paris, Sciences de la vie/Life sciences* 316: 1194-1199.

Becker D, Brettschneider R, Lorz H (1994) Fertile transgenic wheat from microprojectile bombardment of scutellar tissue. *Plant J.* 5: 299-307.

Collakova E, DellaPenna D (2001) Isolation and functional analysis of homogentisate phytyltransferase from *Synechocystis* sp. PCC 6803 and *Arabidopsis. Plant Physiol* 127: 1113-1124.

Datla R, Anderson J W, Selvaraj G (1997) Plant promoters for transgene expression. *Biotechnology Annual Review* 3: 269-296.

DeBlock M, DeBrouwer D, Tenning P (1989) Transformation of *Brassica napus* and *Brassica oleracea* using *Agrobacterium tumefaciens* and the expression of the bar and neo genes in the transgenic plants. *Plant Physiol.* 91: 694-701.

Depicker A, Montagu M V (1997) Post-transcriptional gene silencing in plants. *Curr Opin Cell Biol.* 9: 373-82.

Fellermeier M, Zenk M H. (1998) Prenylation of olivetolate by a hemp transferase yields cannabigerolic acid, the precursor of tetrahydrocannabinol. *FEBS Letters.* 427: 283-285.

Helliwell C A, Waterhouse P M (2005) Constructs and methods for hairpin RNA-mediated gene silencing in plants. *Methods Enzymology* 392:24-35.

Henikoff S, Till B J, Comai L (2004) TILLING. Traditional mutagenesis meets functional genomics. *Plant Physiol* 135:630-6.

Katavic V, Haughn G W, Reed D, Martin M, Kunst L (1994) In planta transformation of *Arabidopsis thaliana. Mol. Gen. Genet.* 245: 363-370.

Katsuyama Y, Funa N, Miyahisa I, Horinouchi S (2007) Synthesis of unnatural flavonoids and stilbenes by exploiting the plant biosynthetic pathway in *Escherichia coli. Chem Biol.* 14(6): 613-21.

Kichikai K, Taura F, Morimoto S, Masayama Y. (2001) Japanese Patent Publication 2001-029082 published Feb. 6, 2001.

Leonard E, Yan Y, Fowler Z L, Li Z, Lim C G, Lim K H, Koffas M A (12 Mar. 2008) Strain Improvement of Recombinant *Escherichia coli* for Efficient Production of Plant Flavonoids. *Mol Pharm.* [Epub ahead of print] PMID: 18333619 [PubMed—as supplied by publisher].

Meyer P (1995) Understanding and controlling transgene expression. *Trends in Biotechnology,* 13: 332-337.

Moloney M M, Walker J M, Sharma K K (1989) High efficiency transformation of *Brassica napus* using *Agrobacterium* vectors. *Plant Cell Rep.* 8: 238-242.

Morimoto S, Komatsu K, Taura F, Shoyama, Y. (1998) Purification and characterization of cannabichromenic acid synthase from *Cannabis sativa. Phytochemistry.* 49: 1525-1529.

Nehra N S, Chibbar R N, Leung N, Caswell K, Mallard C, Steinhauer L, Baga M, Kartha K K (1994) Self-fertile transgenic wheat plants regenerated from isolated scutellar tissues following microprojectile bombardment with two distinct gene constructs. *Plant J.* 5: 285-297.

Ohyanagi H, Tanaka T, Sakai H, Shigemoto Y, Yamaguchi K, Habara T, Fujii Y, Antonio B A, Nagamura Y, Imanishi T, Ikeo K, Itoh T, Gojobori T, Sasaki T. (2008) GenBank Accession NP_001060083.

Page J E, Nagel J (2006) Biosynthesis of terpenophenolics in hop and *cannabis.* In J T Romeo, ed, *Integrative Plant Biochemistry,* Vol. 40. Elsevier, Oxford, pp 179-210.

Potrykus I (1991) Gene transfer to plants: Assessment of published approaches and results. Annu. Rev. Plant Physiol. *Plant Mol. Biol.* 42: 205-225.

Pouwels et al., *Cloning Vectors. A Laboratory Manual,* Elsevier, Amsterdam (1986).

Ralston L, Subramanian S, Matsuno M, Yu O (2005) Partial reconstruction of flavonoid and isoflavonoid biosynthesis in yeast using soybean type I and type II chalcone isomerases. *Plant Physiol.* 137(4): 1375-88.

Rhodes C A, Pierce D A, Mettler I J, Mascarenhas D, Detmer J J (1988) Genetically transformed maize plants from protoplasts. *Science* 240: 204-207.

Sambrook et al, *Molecular Cloning: A Laboratory Manual, Third Edition,* Cold Spring Harbor, N.Y. (2001).

Sanford J C, Klein T M, Wolf E D, Allen N (1987) Delivery of substances into cells and tissues using a particle bombardment process. *J. Part. Sci. Technol.* 5: 27-37.

Schwab R, Ossowski S, Riester M, Warthmann N, Weigel D (2006) Highly specific gene silencing by artificial microRNAs in *Arabidopsis. Plant Cell* 18:1121-33.

Shimamoto K, Terada R, Izawa T, Fujimoto H (1989) Fertile transgenic rice plants regenerated from transformed protoplasts. *Nature* 338: 274-276.

Shoyama Y, Hirano H, Nishioka I. (1984) Biosynthesis of propyl cannabinoid acid and its biosynthetic relationship with pentyl and methyl cannabinoid acids. *Phytochemistry.* 23(9): 1909-1912.

Sirikantaramas S, Morimoto S, Shoyama Y, Ishikawa Y, Wada Y, Shoyama Y, Taura F. (2004) The gene controlling marijuana psychoactivity: molecular cloning and heterologous expression of Delta1-tetrahydrocannabinolic acid synthase from *Cannabis sativa* L. *J Biol Chem.* 279: 39767-39774.

Sirikantaramas S, Taura F, Tanaka Y, Ishikawa Y, Morimoto S, Shoyama Y. (2005) Tetrahydrocannabinolic acid synthase, the enzyme controlling marijuana psychoactivity, is secreted from the storage cavity of the glandular trichomes. *Plant Cell Physiol.* 46: 1578-1582.

Songstad D D, Somers D A, Griesbach R J (1995) Advances in alternative DNA delivery techniques. *Plant Cell, Tissue and Organ Culture* 40:1-15.

Stam M, de Bruin R, van Blokland R, van der Hoorn R A, Mol J N, Kooter J M (2000) Distinct features of post-transcriptional gene silencing by antisense transgenes in single copy and inverted T-DNA repeat loci. *Plant J.* 21:27-42.

Taura F, Morimoto S, Shoyama Y. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. *J Biol Chem.* 271: 17411-17416.

Taura F, Morimoto S, Shoyama Y, Mechoulam R. (1995) First direct evidence for the mechanism of 1-tetrahydrocannabinolic acid biosynthesis. *Journal of the American Chemical Society.* 117: 9766-9767.

Taura F, Matsushita H, Morimoto S, Masayama Y. (2000) Japanese Patent Publication 2000-078979 published Mar. 21, 2000.

Taura F, Sirikantaramas S, Shoyama Y, Yoshikai K, Shoyama Y, Morimoto S. (2007) Cannabidiolic-acid synthase, the chemotype-determining enzyme in the fiber-type *Cannabis sativa. FEBS Lett.* 581: 2929-2934.

Taura F, Tanaka S, Taguchi C, Fukamizu T, Tanaka H, Shoyama Y, Morimoto, S. (2009) Characterization of olivetol synthase, a polyketide synthase putatively involved in cannabinoid biosynthetic pathway. *FEBS Lett.* 583: 2061-2066.

Vasil I K (1994) Molecular improvement of cereals. *Plant Mol. Biol.* 25: 925-937.

Walden R, Wingender R (1995) Gene-transfer and plant regeneration techniques. *Trends in Biotechnology* 13: 324-331.

Zhang H, Wang Y, Pfeifer B A (31 Jan. 2008) Bacterial hosts for natural product production. *Mol Pharm.* [Epub ahead of print] PMID: 18232637 [PubMed—as supplied by publisher].

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An isolated or purified nucleic acid molecule comprising a nucleotide sequence having:
   i) at least 95% sequence identity to SEQ ID NO: 1,
   ii) the sequence as set forth in SEQ ID NO:1,
   iii) a nucleotide sequence encoding an isolated polypeptide having at least 95% sequence identity to SEQ ID NO: 2,
   iv) a nucleotide sequence encoding an isolated polypeptide having the sequence as set out in SEQ ID NO: 2 or a conservatively substituted sequence thereof; or
   v) a codon degenerate sequence of i), ii), iii) or iv),
wherein i), ii), iii), iv) and v) encode a polypeptide having aromatic prenyltransferase activity and wherein the nucleic acid molecule is a cDNA and/or contains at least one non-naturally occurring substitution modification relative to SEQ ID NO:1.

2. An isolated or purified polypeptide comprising an amino acid sequence having:
   i) at least 95% sequence identity to SEQ ID NO: 2,
   ii) the sequence as set out in SEQ ID NO: 2, or
   iii) a conservatively substituted amino acid sequence of i) or ii);
having aromatic prenyltransferase activity and containing at least one non-naturally occurring substitution modification relative to SEQ ID NO:2.

3. A vector, construct or recombinant expression system comprising a nucleic acid molecule comprising:
   i) a nucleotide sequence having at least 95% sequence identity to SEQ ID NO: 1,
   ii) a nucleotide sequence having the sequence as set forth in SEQ ID NO:1,
   iii) a nucleotide sequence encoding an isolated polypeptide having at least 95% sequence identity to SEQ ID NO: 2,
   iv) a nucleotide sequence encoding an isolated polypeptide having the sequence as set out in SEQ ID NO: 2; or
   v) a codon degenerate sequence of any one of i) to iv),
wherein i), ii), iii), iv) and v) encode a polypeptide having aromatic prenyltransferase activity.

4. An in vitro process of transferring a prenyl group comprising: reacting a prenyl group acceptor molecule with a prenyl group donor molecule in the presence of an aromatic prenyltransferase polypeptide comprising an amino acid sequence having:
   i) at least 95% sequence identity to SEQ ID NO: 2,
   ii) the sequence as set out in SEQ ID NO: 2, or
   iii) a conservatively substituted amino acid sequence of i) or ii);
wherein the aromatic prenyltransferase polypeptide catalyzes the transfer of the prenyl group from the prenyl group donor molecule to the prenyl group acceptor molecule.

5. A method of decreasing levels of cannabinoid compounds in a *cannabis* plant, *cannabis* cell or *cannabis* tissue comprising expressing the nucleic acid molecule as defined in claim 1 i) to iii) or a part thereof to silence expression of the aromatic prenyltransferase gene in the *cannabis* plant, *cannabis* cell or *cannabis* tissue, in comparison to a *canna-* bis plant, *cannabis* cell or *cannabis* tissue grown without the use of the nucleic acid molecule for silencing.

6. An in vitro method of increasing levels of cannabinoid compounds in a cell comprising expressing or over-expressing the nucleic acid molecule as defined in claim 1 i) to v) in the cell, in comparison to a cell of the same species not expressing or over-expressing the nucleic acid molecule.

7. An in vitro method of increasing levels of cannabinoid compounds in a cell comprising expressing or over-expressing a nucleic acid molecule encoding the polypeptide as defined in claim 2 in the cell, in comparison to a cell of the same species not expressing or over-expressing the nucleic acid molecule.

8. The method of claim 6, wherein the cell is or is from a microorganism, an insect cell or a plant cell.

9. The method of claim 8, wherein the microorganism is yeast or *E. coli* or the insect cell is a *Spodoptera frugiperda* cell.

10. The method of claim 6, wherein the nucleic acid molecule is expressed or over-expressed in combination with expression or over-expression of one or more other nucleic acids that encode one or more enzymes in a cannabinoid biosynthetic pathway.

11. The method of claim 10, wherein the one or more enzymes in the cannabinoid biosynthetic pathway is one or more of $\Delta^9$-tetrahydrocannabinolic acid synthase, cannabidiolic acid synthase and cannabichromenic acid synthase.

12. The process of claim 4, wherein the aromatic prenyltransferase is in a membrane preparation.

13. The process of claim 12, wherein the membrane preparation is obtained by expressing the aromatic prenyltransferase in a cell and obtaining the membrane fraction of the cell, optionally by sonicating the cell.

14. The process of claim 13, wherein the cell is a yeast cell or an insect cell.

15. The process of claim 13, wherein the step of expressing the aromatic prenyltransferase comprises transforming the cell with a vector, construct or virus.

16. The process of claim 7, wherein the prenyl group donor molecule is geranyl disphosphate and/or the prenyl group acceptor molecule is olivetolic acid.

17. The process of claim 12, wherein the membrane preparation further comprises one or more other enzymes in a cannabinoid biosynthetic pathway.

18. The process of claim 17, wherein the one or more other enzymes in a cannabinoid biosynthetic pathway is one or more of $\Delta^9$-tetrahydrocannabinolic acid synthase, cannabidiolic acid synthase and cannabichromenic acid synthase.

19. A membrane preparation comprising the polypeptide of claim 2.

20. The membrane preparation of claim 19, prepared from a recombinant cell expressing the polypeptide.

21. A cell expressing the polypeptide of claim 2.

22. A recombinant cell comprising the vector, construct or recombinant expression system of claim 3.

* * * * *

UNITED STATES PATENT AND TRADEMARK OFFICE
CERTIFICATE OF CORRECTION

PATENT NO. : 9,765,308 B2
APPLICATION NO. : 14/510232
DATED : September 19, 2017
INVENTOR(S) : Jonathan E. Page and Zakia Boubakir It is certified that error appears in the above-identified patent and that said Letters Patent is hereby corrected as shown below:

In the Claims

Claim 16 should read:
16. The process of claim 4, wherein the prenyl group donor molecule is geranyl disphosphate and/or the prenyl group acceptor molecule is olivetolic acid.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*